(12) United States Patent
Bernier et al.

(10) Patent No.: US 8,207,157 B2
(45) Date of Patent: Jun. 26, 2012

(54) METHODS AND COMPOSITIONS FOR REPELLING ARTHROPODS

(75) Inventors: Ulrich R. Bernier, Gainesville, FL (US);
Kenneth Posey, Gainesville, FL (US);
Daniel L. Kline, Gainesville, FL (US);
Donald Barnard, Gainesville, FL (US);
Kamal Chauhan, Laurel, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1205 days.

(21) Appl. No.: 11/953,343

(22) Filed: Dec. 10, 2007

(65) Prior Publication Data
US 2008/0188456 A1 Aug. 7, 2008

Related U.S. Application Data

(60) Provisional application No. 60/877,464, filed on Dec. 28, 2006.

(51) Int. Cl.
| A01N 43/36 | (2006.01) |
| A01N 43/62 | (2006.01) |
| A01N 43/60 | (2006.01) |
| A01N 43/40 | (2006.01) |
| A01N 43/50 | (2006.01) |
| A01N 43/84 | (2006.01) |
| A01N 43/46 | (2006.01) |
| A01P 7/00 | (2006.01) |

(52) U.S. Cl. ............ 514/212.01; 514/218; 514/408; 514/252.12; 514/315; 514/385; 514/227.5; 514/231.2

(58) Field of Classification Search .............. None
See application file for complete search history.

(56) References Cited

U.S. PATENT DOCUMENTS

| 6,147,091 | A * | 11/2000 | Kruger et al. ............. 514/315 |
| 6,362,235 | B1 | 3/2002 | Nolen et al. |
| 6,953,814 | B2 | 10/2005 | Reifenrath |
| 2006/0069083 | A1 * | 3/2006 | Steiner et al. ............. 514/211.11 |
| 2008/0188456 | A1 * | 8/2008 | Bernier et al. ............. 514/212.01 |

OTHER PUBLICATIONS

Definition of "arthropod" in Webster's Dictionary, obtained May 19, 2011.*
Data sheet from the Chemical Book. 2010; homopiperizine: 505-66-8.*
Bernier, U. et al., "Human Emanations and Related Natural Compounds that Inhibit Mosquito Host-Finding Abilities", In Insect Repellents: Principles, Methods and Uses, Debboun, M., Frances, S. Strickman, D., (Eds.), 2006, pp. 77-100.
Bernier, U. et al., "Analysis of Human Skin Emanations by Gas Chromatography/Mass Spectrometry. 2. Identification of Volatile Compounds that are Candidate Attractants for the Yellow Fever Mosquito (Aedes aegypti)", Analytical Chemistry, vol. 72, (4), 2000, pp. 747-756.
Bernier, U. et al., "Chemical Analysis of Human Skin Emanations: Comparison of Volatiles from Humans that Differ in Attraction of Aedes aegypti (Diptera: Culicidae)", J. of the American Mosquito Control Association, vol. 18, (3), 2002, pp. 186-195.
Bernier, U. et al., "Comparison of Contact and Spatial Repellency of Catnip Oil and N,N-Diethyl-3-methylbenzamide (Deet) Against Mosquitoes", J. of Medical Entomology, vol. 42, (3), 2005, pp. 306-311.
Birkett, M. et al., "The Role of Volatile Semiochemicals in Mediating Host Location and Selection by Nuisance and Disease-Transmitting Cattle Flies", Medical and Veterinary Entomology, vol. 18, 2004, pp. 313-322.
Bosch, O. et al., "Contribution of Fatty Acids to Olfactory Host Finding of Female-Aedes aegypti", Chem. Senses, vol. 25, 2000, pp. 323-330.
Costantini, C. et al., "Electroantennogram and Behavioural Responses of the Malaria Vector Anopheles gambiae to Human-Specific Sweat Components", Medical and Veterinary Entomology, vol. 15, 2001, pp. 259-266.
Douglas III, H. et al., "Heteropteran Chemical Repellents Identified in the Citrus Odor of a Seabird (Crested Auklet: Aethia cristatella): Evolutionary Convergence in Chemical Ecology", Naturwissenschaften, vol. 88, 2001, pp. 330-332.
Douglas III, H. et al., "Chemical Odorant of Colonial Seabird Repels Mosquitoes", J. of Medical Entomology, vol. 42, (4), 2005, pp. 647-651.
Douglas III, H. et al., "Interspecific Differences in Aethia Spp. Auklet Odorants and Evidence for Chemical Defense Against Ectoparasites", J. of Chemical Ecology, vol. 30, (10), 2004, pp. 1921-1934.
Gouck, H. et al., "Chemicals Tested as Space repellents Against Yellow-Fever Mosquitoes. I. Esters", J. of Economic Entomology, vol. 60, (6), 1967, pp. 1587-1590.

(Continued)

Primary Examiner — Shanon A Foley
(74) Attorney, Agent, or Firm — John D. Fado; G. Byron Stover

(57) ABSTRACT

A method for repelling arthropods involving treating an object or area with an arthropod repelling effective amount of at least one compound having the formula

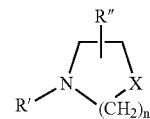

wherein X is O, S, NH, N-NH$_2$, N-CH$_3$ or CH$_2$, R' is H or alkyl, R" is alkyl, n is 0, 1, 2, 3 or 4, and mixtures thereof, optionally including a carrier material or carrier. The compound is preferably selected from homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methlyhomopiperidine, or mixtures thereof.

11 Claims, 4 Drawing Sheets

OTHER PUBLICATIONS

Kline, D. et al., "Olfactometric Evaluation of Spatial Repellents for *Aedes aegypti*", *J. of Med. Entomol.*, vol. 40, (4), 2003, pp. 463-467.

Torr, S. et al., "Response of Glossina Pallidipes (Diptera: Glossinidae) to Synthetic Repellents in the Field", *Bulletin of Entomological Research*, vol. 86, 1996, pp. 609-616.

Schreck, C. et al., "Spatial Action of Mosquito Repellents", *J. of Economic Entomology*, vol. 63, (5), 1970, pp. 1576-1578.

Skinner, W. et al., "Repellency of Skin-Surface Lipids of Humans to Mosquitoes", *Science, New Series*, vol. 149, (3681), 1965, pp. 305-306.

Smallengange, R. et al., "Synergism Between Ammonia, Lactic Acid and Carboxylic Acids as Kairomones in the Host-Seeking Behaviour of the Malaria Mosquito *Anopheles gambiae* Sensu Stricto (Diptera: Culicidae)", *Chem. Senses*, vol. 30, 2005, pp. 145-152.

Wirtz, R. et al., "Mosquito Area Repellents: Laboratory Testing of Candidate Materials Against *Aedes aegypti*", *Mosquito News*, vol. 40, (3), 1980, pp. 432-439.

Wright, R. et al., "Insects Attractants, Anti-Attractants, and Repellents", *The Canadian Entomologist*, vol. 103, 1971, pp. 627-630.

\* cited by examiner

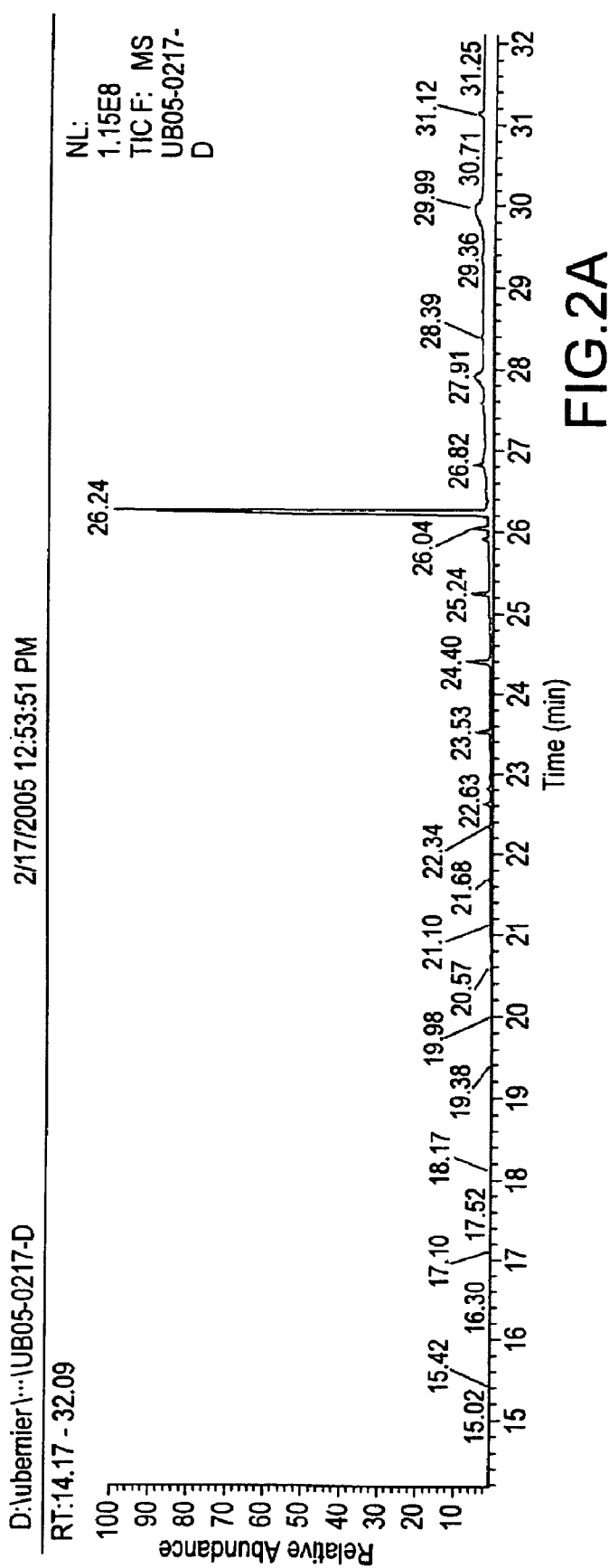

METHODS AND COMPOSITIONS FOR REPELLING ARTHROPODS

REFERENCE TO RELATED APPLICATION

This application claims the benefit of U.S. Provisional Application No. 60/877,464, filed 28 Dec. 2006, which is incorporated herein by reference in its entirety.

BACKGROUND OF THE INVENTION

The present invention relates to a method for repelling arthropods involving treating an object or area with an arthropod repelling effective amount of at least one compound having the formula

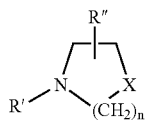

wherein X is O, S, NH, N-NH$_2$, N-CH$_3$ or CH$_2$, R' is H or alkyl, R" is alkyl, n is 0, 1, 2, 3 or 4, and mixtures thereof, optionally including a carrier material or carrier. The compound is preferably homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylbomopiperidine, or mixtures thereof.

Insect repellants are widely used throughout the United States and throughout the world. In some regions, the use of insect repellants is critical to avoiding or reducing the occurrence of disease carried by insects. For example the Centers for Disease Control (CDC) receives nearly 10,000 reports of Lyme disease (transmitted by deer ticks) and 1,000 reports of encephalitis (transmitted by mosquitoes) annually.

Currently, the most common insect repellent is N,N-diethyl-meta-toluamide (DEET). DEET was designed to be applicable to the skin of subjects, and was designed to repel rather than kill insects. Although in use for some time, concern has recently emerged about the potential toxicity of DEET to children. Recently the US Environmental Protection Agency (EPA) determined that it would no longer allow child safety claims on labels for DEET-containing products.

Thus there is a need for alternatives to chemicals such as DEET as novel personal protectants for use against arthropods such as mosquitoes.

SUMMARY OF THE INVENTION

In accordance with the present invention there is provided a method for repelling arthropods involving treating an object or area with an arthropod repelling effective amount of at least one compound having the formula

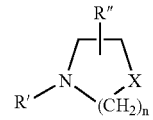

wherein X is O, S, NH, N-NH$_2$, N-CH$_3$ or CH$_2$, R' is H or alkyl, R" is alkyl, n is 0, 1, 2, 3 or 4, and mixtures thereof, optionally including a carrier material or carrier.

Also in accordance with the present invention, there is provided a method for repelling arthropods involving treating an object or area with an arthropod repelling effective amount of at least one compound selected from homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylhomopiperidine, or mixtures thereof, optionally including a carrier material or carrier.

DETAILED DESCRIPTION OF THE INVENTION

Figure 1A:
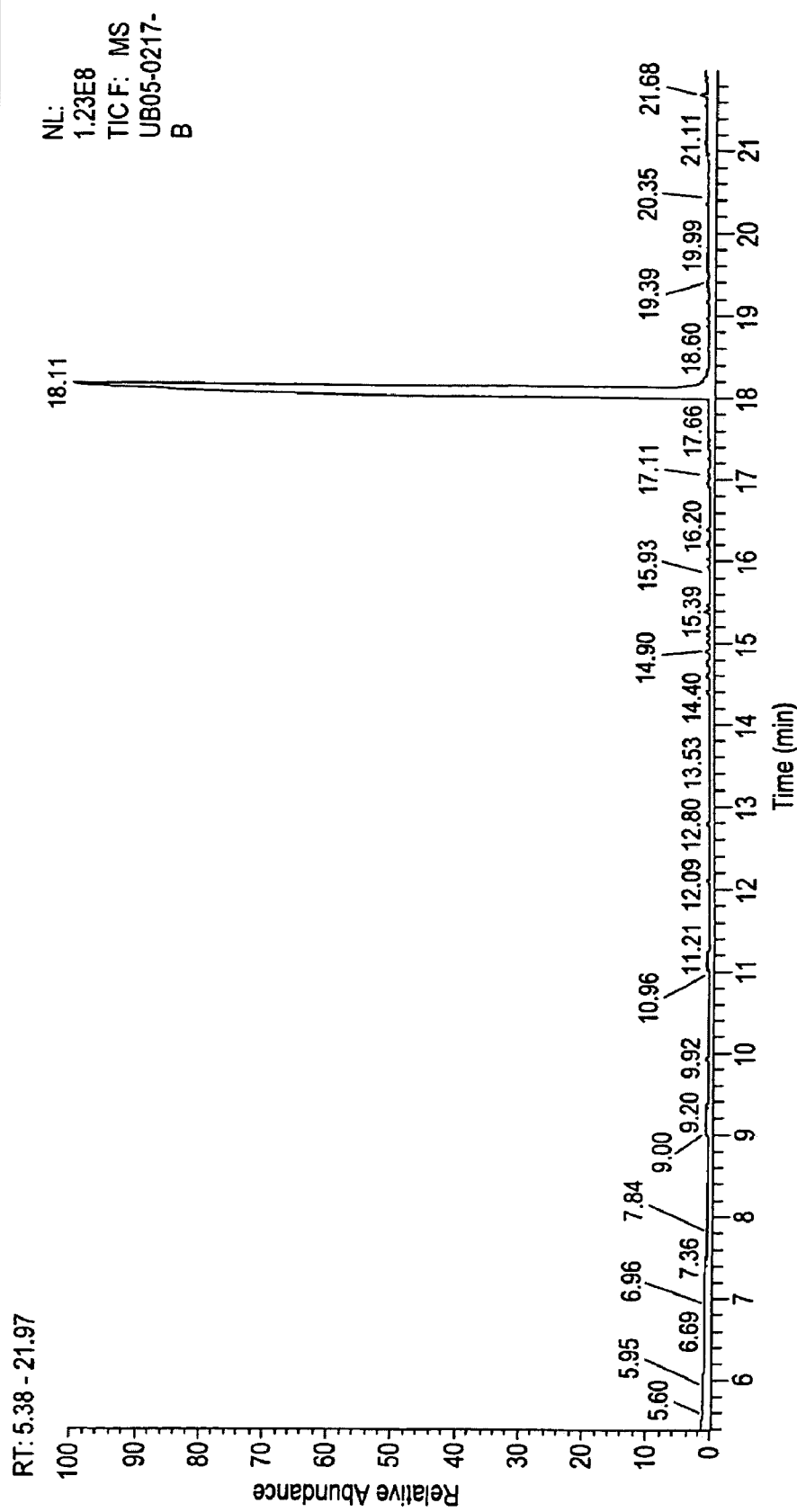
FIGS. 1 A and B and FIGS. 2 A and B respectively show mass spectra of synthetic standards: UB 05-217-B is 1-methyl-4-octyl piperazine, UB 05-217-D is 4-cyclohex-3-en-1-one-1-methylpiperazine.

We have found compounds which produce a spatial repellent effect when released into the environment. Without being bound by theory, these agents result in masking attractive odors from insects that normally would be receptive to the attractants by producing anosmia or hyposmia in the insects.

The present invention relates to a method for repelling arthropods involving treating (or exposing) an object (e.g., mammals such as humans) or area (e.g., a surface such as human skin) with an arthropod repelling effective amount of at least one compound having the formula

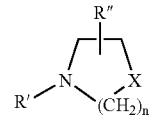

wherein X is O, S, NH, N-NH$_2$, N-CH$_3$ or CH$_2$, R' is H or alkyl (e.g., C$_{1-10}$, preferably C$_{1-2}$), R" is alky (e.g., C$_{1-10}$, preferably C$_{1-2}$), n is 0, 1, 2, 3 or 4, and mixtures thereof, optionally including a carrier material or carrier. Preferably the compound is selected from homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6- dimethylpiperazine, 2,5-dimethylpiperazine, piperazine, 1-methylhomopiperidine, or mixtures thereof.

The terms "object" or "area" as used herein include any place where the presence of target pests is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing. Thus the invention includes dispensing the compounds described herein into the environment in vapor form (e.g., an aerosol) preferably using devices that allow a slow sustained release of these compounds into the environment from a sealed canister.

A composition is disclosed for repelling arthropods, containing at least two compounds having the formula

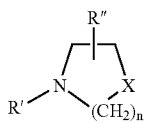

wherein X is O, S, NH, N-NH$_2$, N-CH$_3$ or CH$_2$, R' is H or alkyl, R" is alkyl, n is 0, 1, 2, 3 or 4. Preferably the composition contains at least two compounds selected from homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylhomopiperidine, or mixtures thereof, optionally including a carrier material or carrier.

The compositions and compounds, and methods of using them, can therefore be used for repelling harmful or troublesome arthropods such as blood-sucking and biting insects, ticks and mites.

The blood-sucking insects include mosquitoes (for example *Aedes*, *Culex* and *Anopheles* species), sand flies (for example *Phlebotomus* and *Lutzomtyia* species), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus*, *Haematopota* and *Chrysops* species), house flies (for example *Musca domestica* and *Fannia canicularis*), meat flies (for example *Sarcophaga carnaria*), black flies (*Prosimuliim mixtum*, *Cnephia pecuarum*, *Simuliim vittatum*), flies which cause myiasis (for example *Lucilia cuprina*, *Chrysomyia chloropyga*, *Hypoderma bovis*, *Hypoderma lineatum*, *Derniatobia hominis*, *Oestrus ovis*, *Gasterophilus intestinalis* and *Cochliomyia hominovorax*), bugs (for example *Cimex lectularius*, *Rhodnius prolixus* and *Triatoma infestans*), lice (for example *Pediculus humanus*, *Haematopinus suis* and *Damalina ovis*), louse flies (for example *Melaphagus orinus*), fleas (for example *Pulex irritans*, *Cthenocephalides canis* and *Xenopsylla cheopis*) and sand fleas (for example *Dermatophilus penetrans*).

The biting insects include cockroaches (for example *Blattella germanica*, *Periplaneta americana*, *Blatta orientalis* and *Supella supellectilium*), beetles (for example *Sitophilus granarius*, *Tenebrio molitor*, *Dermestes lardarius*, *Stegobium paniceum*, *Anobium puntactum* and *Hylotrupes bajulus*), termites (for example *Reticulitermes lucifugus*) and ants (for example *Lasius niger*).

The ticks include, for example, *Ornithodorus moubata*, *Ixodes ricinus*, *I. scapularis*, *Boophilus microplus*, *Dermacentor variabilis*, *D. andersoni*, *Hyalomma marginatum*, *H. anatolicum*, *Amblyomma hebreum*, and *A. americanum*, and mites include, for example, *Sarcoptes scabiei* and *Dermanyssus gallinae*.

The compounds according to the invention, which can be used in undiluted or diluted form, can be converted into formulations customary for repellents. They can be used in all the presentation forms customary in cosmetics, for example in the form of solutions, emulsions, gels, ointments, pastes, creams, powders, sticks, sprays or aerosols from spray cans.

For use in the non-cosmetic sector, the compounds can be incorporated, for example, into granules, oily spraying agents or slow release formulations.

The formulations are prepared in a known manner by mixing or diluting the compounds according to the invention with solvents (for example xylene, chlorobenzenes, paraffins, methanol, ethanol, isopropanol or water), carriers (for example kaolins, aluminas, talc, chalk, highly disperse silicic acid and silicates, nanoclays), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compounds according to the invention can be mixed with one another in the formulations or can also be used as mixtures with other known active compounds (for example sunscreen agents). The formulations in general contain between about 0.1 and about 95% (e.g., 0.1-95%) by weight of active compound, preferably between about 0.5 and about 90% (e.g., 0.5-90%).

For protection from arthropods such as blood-sucking insects or mites, the compounds according to the invention are generally either applied to human or animal skin, or items of clothing and other objects are treated with the compounds. Preferably, the compounds are dispensed into the environment (e.g., outdoors or indoors) in vapor form (e.g., an aerosol).

The compounds according to the invention are also suitable as an additive to impregnating agents for, for example, textile webs, articles of clothing and packaging materials, and as an additive to polishing, cleaning and window-cleaning agents.

The compositions of the present invention contain a carrier and the compound. The repellent of the present invention is generally applied with a carrier component. The carrier component can be a liquid or a solid material. As is known in the art, the vehicle or carrier to be used refers to a substrate such as a gel, polymers, or the like. All of these substrates have been used to release insect repellents and are well known in the art.

The compounds herein are described as repellents because they result in a reduction in the ability of insects to locate a host, and thus reduce the incidence of biting. Generally, an insect repellant is any compound or composition which deters insects from a host, thus the term "repelling" is defined as causing arthropods (e.g., *Aedes aegypti*) to make oriented movements away from a source of a chemical repellent (Dethier, V. L., et al., J. Econ. Ent., 53: 134-136 (1960)) but also includes inhibiting feeding by arthropods when a chemical is present in a place where insects would, in the absence of the chemical, feed. Thus the term "repelling" also includes reducing the number of arthropod (e.g., *Aedes aegypti*) bites on a treated area or object (e.g., mammalian skin which has been treated topically with the compositions or compounds of the present invention) when compared to the same area or object which is untreated.

The amount of the compound used will be at least an effective amount. The term "effective amount," as used herein, means the minimum amount of the compound needed to reduce the ability of insects to locate a host and thus reduce the incidence of biting, or to cause arthropods to make oriented movements away from a treated area or object (e.g., mammalian skin which has been treated topically with the compound of the present invention) when compared to the same area or object which is untreated. The term "effective amount," as used herein, also means the minimum amount of the compound needed to reduce the number of arthropod (e.g., *Aedes aegypti*) bites on a treated area or object (e.g., mammalian skin which has been treated topically with the compound of the present invention) when compared to the same area or object which is untreated. Effective concentrations of the compound in the compositions may vary between about 0.1 and about 95% (e.g., (0.1-95%) by weight, preferably between about 0.5 and about 90% (e.g., 0.5-90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

The compounds may be used with other repellents or arthropod control agents (e.g., insecticides, chemosterilants or the like). When used, these agents should be used in an amount which, as readily determined by one skilled in the arts, will not interfere with the effectiveness of the compound.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Non-competitive tests were conducted to demonstrate the reduction in "absolute" attraction mean±SE (%) from the addition of 50 μL 1-methylpiperazine (1-MPZ) to odors from a human volunteer's arm/hand and to 1 mL of a synthetic 3-compound odor blend (1 g L-lactic acid dissolved in 498 mL acetone and 2 mL dimethyl disulfide). All chemicals and blends were released from a plastic absorbent support. Approximately 75 female *Aedes aegypti* mosquitoes were used for each repetition.

TABLE 1

| Attractant | without 1-MPZ mean ± SE (%) | with 50 μL 1-MPZ mean ± SE (%) |
|---|---|---|
| Blend | 92.7 ± 1.6 | 12.8 ± 1.8 |
| Human Odor | 88.6 ± 1.7 | 23.5 ± 3.0 |

The data in Table 1 indicated that addition of 1-methylpiperzine (1-MPZ) to kairomones, whether natural human odors or a standard synthetic human odor blend, reduced the attraction to the odor source. Bioassays were conducted for 3 min. It was clear that both the blend and human odor were highly attractive in this bioassay. The addition of a small amount of 1-MPZ to the port with the odor source surprisingly produced a significant reduction in absolute attraction.

Competitive tests were conducted (partly to demonstrate the applicability of the compounds in a "push-pull" system) using a synthetic blend and odors from the arm/hand of a human volunteer and which illustrated that the addition of 1-methylpiperazine (1-MPZ, 50 μL) not only inhibited female *Ae. aegypti*, but also shifted the preference away from humans to a synthetic blend. Furthermore, the presence of the inhibitor reduced the overall total catch of mosquitoes to both ports of the laboratory olfactometer used for bioassays.

TABLE 2

| Treatment 1 | Attraction ± SE (%) | Treatment 2 | Attraction ± SE (%) | Total Catch (%) |
|---|---|---|---|---|
| Human Odor | 84.6 ± 4.1 | Blend | 12.6 ± 3.5 | 97.2 |
| Human + 1-MPZ | 29.5 ± 3.2 | Blend | 48.6 ± 3.8 | 78.1 |

The data in Table 2 showed that in a competitive test, human odors can be compared against the blend by placing each treatment in a separate port and passing air over the treatments. Mosquitoes choose to fly upwind into a port with the treatment or choose to remain in the cage. It is clear that in competition, these mosquitoes preferred the natural human odors over the blend by about a 5:1 margin. However, when 1-MPZ was introduced into the port containing the human odors, the mosquitoes surprisingly shifted their preference to the blend. A second impact was that surprisingly fewer mosquitoes (97.2% compared to 78.1%) responded to the odor source, indicating that anosmia or hyposmia resulted in the insects from the presence of the inhibitor.

Non-competitive determination of absolute attraction±SE (%) to attractants and attractants combined with candidate inhibitors was conducted. Treatments consisted of odors from the human arm/hand, catnip oil at a dose of 50 μL, 1-methylpiperazine (1-MPZ) at a dose of 50 μL, and a 500 μL aliquot of the 3-compound synthetic blend on a plastic polymer support. Data were analyzed by Newman-Keuls Multiple Comparisons test to evaluate the separation of the means. Values with different letters are significantly different at the 95% confidence level.

TABLE 3

| Treatment | Attraction mean ± SE (%) |
|---|---|
| Human Odors | 82.8(a) ± 3.0 |
| Human Odors + Catnip Oil | 62.2(b) ± 4.7 |
| Human Odors + Catnip Oil + 1-MPZ | 25.2(c) ± 3.7 |
| Right Hand Odors + 1-MPZ | 20.9(cd) ± 2.6 |
| Catnip Oil | 15.5(cd) ± 2.1 |
| Catnip Oil + 1-MPZ | 14.4(cd) ± 1.7 |
| 1-MPZ | 7.6(d) ± 1.5 |
| Blank | 3.8(d) ± 0.4 |
| Blend | 67.5(b) ± 3.3 |
| Blend + Catnip Oil | 24.8(c) ± 6.4 |
| Blend + Catnip Oil + 1-MPZ | 11.4(d) ± 1.3 |
| Blend + 1-MPZ | 8.2(d) ± 1.5 |

The data in Table 3 demonstrated that compounds in catnip oil impart a vapor phase effect on mosquitoes which resulted in a statistically significant reduction in attraction to both types of kairomonal odors (the blend and the human hand/arm). The addition of 1-methylpiperazine surprisingly resulted in a further statistically significant reduction in attraction over that provided by the catnip oil. However, addition of catnip oil did not increase the ability of 1-MPZ to produce anosinia in a greater number of mosquitoes.

TABLE 4

Comparison of paired treatments in competitive tests demonstrated the effect of candidate inhibitors when added to one of a pair of identical treatments. LH = Odors from the left hand and arm of a human volunteer, RH = right hand/arm odors of the same human volunteer used throughout data acquisition for this study. The blend was the 3-compound blend described previously, C is catnip oil at 50 μL, 1-MPZ is 1-methylpiperazine at 50 μL. Data analyzed by paired t-tests, *indicates a significant difference at the 0.05 level does not exist.

| Treatment without Inhibitor | Attraction mean ± SE (%) | Treatment with Inhibitor | Attraction mean ± SE (%) | t | P |
|---|---|---|---|---|---|
| LH | 47.3 ± 4.3 | RH + C | 24.9 ± 3.6 | 5.89 | 0.002 |
| LH | 23.9 ± 3.1 | RH + C + 1-MPZ | 8.5 ± 2.1 | 4.61 | 0.0058 |
| LH | 25.9 ± 4.2 | RH + 1-MPZ | 7.7 ± 1.2 | 4.27 | 0.0079 |
| Blend* | 35.9 ± 11.6 | Blend + C* | 5.9 ± 1.5 | 2.30 | 0.0695 |
| Blend | 13.7 ± 1.2 | Blend + C + 1-MPZ | 2.8 ± 1.0 | 8.51 | <0.001 |
| Blend | 8.9 ± 2.5 | Blend + 1-MPZ | 3.4 ± 1.0 | 2.62 | 0.0467 |
| Blend | 5.5 ± 1.4 | RH + C | 77.0 ± 4.8 | 11.66 | <0.001 |
| Blend* | 13.6 ± 1.2 | RH + C + 1-MPZ* | 15.4 ± 3.8 | 0.40 | 0.7069 |
| Blend* | 16.3 ± 3.0 | RH + 1-MPZ* | 14.1 ± 2.7 | 0.95 | 0.382 |
| RH | 83.9 ± 4.0 | Blend + C | 2.3 ± 1.2 | 22.80 | <0.001 |
| RH | 27.1 ± 4.3 | Blend + C + 1-MPZ | 1.1 ± 0.6 | 5.93 | 0.0019 |
| RH | 37.4 ± 6.0 | Blend + 1-MPZ | 0.9 ± 0.3 | 5.96 | 0.0019 |

In the competitive analysis shown in Table 4, using either identical aliquots of the blend or using the odors fi-om the left and right hand from the same subject, it was apparent that catnip and 1-methylpiperazine (or the combination) significantly inhibited the mosquitoes from locating the odor source that was emitted with these chemicals. Furthermore, the addition of catnip to hand odors (RH+C) did not effectively conceal the human odors and shift the mosquitoes to a preference for blend odors. In contrast, the inclusion of 1-methylpiperazine surprisingly reduced the attraction to human odors to the level where no statistically significant difference was observed in mosquito preference to those combinations or to the blend.

Structures of chemicals used used for Tables 5-8:

| # | Name | Structure |
|---|---|---|
| 1 | 1-Methylpiperazine (1-MPZ) | 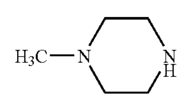 |
| 2 | 4-cyclohex-3-en-1-one-1-methylpiperazine (3-CC-1-MPZ) | 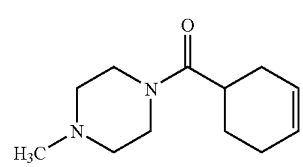 |
| 3 | 1-methyl-4-octylpiperazine (1M-4-OPZ) | 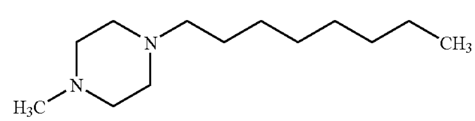 |
| 4 | 4-methylmorpholine (4-MM) | 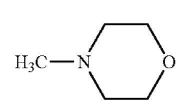 |

Figure 1B:
Figure 2B:
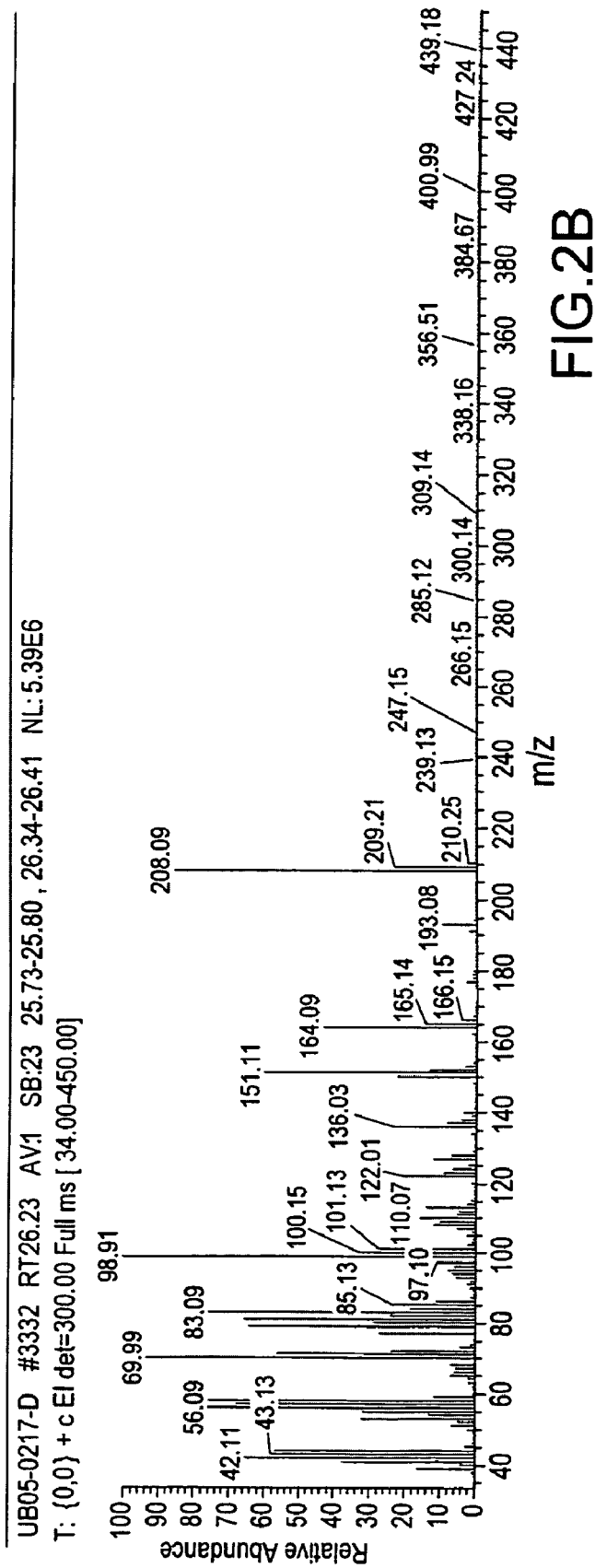

FIGS. 1 A and B and FIGS. 2 A and B respectively show Mass Spectra of synthetic standards: UB 05-217-B is 1-methyl-4-octyl piperazine, UB 05-217-D is 4-cyclohex-3-en-1-one-1-methylpiperazine. These chromatograms confirm the purity of samples synthesized and the mass spectra can be interpreted to confirm the identity. The M+. ions (m/z 212, 208) are the exact relative molecular masses of each compound.

50 µL each of 1-methylipiperazine (1-MPZ), 4-cyclohex-3-en-1-one-1-methylpiperazine (the 3-cyclohexenyl carbonyl analog of 1-MPZ) (3-CC-1-MPZ), 1-methyl-4-octylpiperazine (1M-4-OPZ) and 4-methyl morpholine (4-MM) were evaluated as inhibitors of hand odors compared to 500 µL of the 3 compound blend with *Aedes aegypti* mosquitoes. Results of non-competitive tests with *Aedes aecypti* are shown in Table 5. Separation of means were examined by Newman-Keuls Multiple Comparisons test.

TABLE 5

| Treatment | with hand odors mean ± SE (%) | with blend mean ± SE (%) |
|---|---|---|
| Without Inhibitor | 90.1(a) ± 2.8 | 84.2(a) ± 6.0 |
| +4-cyclohex-3-en-1-one-1-methylpiperazine | 82.1(ab) ± 4.6 | 85.1(a) ± 2.2 |
| +1-methyl-4-octylpiperazine | 66.6(b) ± 10.9 | 59.8(b) ± 9.8 |
| +4-methylmorpholine | 46.0(c) ± 5.9 | 15.2(c) ± 2.6 |
| +1-methylpiperazine + 4-methylmorpholine | 29.0(c) ± 2.7 | 2.2(cd) ± 0.9 |
| +1-methylpiperazine | 28.6(c) ± 5.8 | 4.5(cd) ± 1.2 |
| +1-methylpiperazine + 1-methyl-4-octylpiperazine | 18.1(c) ± 3.1 | 7.8(cd) ± 1.5 |

The data in Table 5 indicated that 1-methylpiperazine surprisingly produced anosmia in mosquitoes more effectively than 1-methyl-4-octylpiperazine and the cyclohexenyl carbonyl analog of 1-methylpiperazine (tested because it is similar in structure to some potent contact repellents). The data also indicated that combination of 1-methyl-4-octylpiperazine with 1-methylpiperazine din not produce in increased level of anosmia or hyposmia in mosquitoes.

1-MPZ was tested to determine whether it could inhibit a different mosquito species, *An. albimanus*, a mosquito that can transmit malaria and is one of the most notorious for feeding readily through repellents. Results are shown in Table 6.

TABLE 6

Evaluation of 50 µL each of 1-methylipiperazine, 4-cyclohex-3-en-1-one-1-methylpiperazine, 1-methyl-4-octylpiperazine, and 4-methyl morpholine (4-MM) as inhibitors of hand odors or with 500 µL of the 3 compound blend.. Results of non-competitive tests with *An. albimanus* mosquitoes are below. Separation of means are examined by Newman-Keuls Multiple Comparisons test.

| Treatment | with hand odors mean ± SE (%) | with blend mean ± SE (%) |
|---|---|---|
| Without Inhibitor | 62.8(a) ± 6.2 | 62.2(a) ± 2.4 |
| +1-methyl-4-octylpiperazine | 56.8(a) ± 4.8 | 55.1(a) ± 8.7 |
| +4-methylmorpholine | 51.7(a) ± 9.6 | 13.8(c) ± 5.4 |
| +1-methylpiperazine + 4-methylmorpholine | 27.0(b) ± 5.6 | 30.2(b) ± 2.1 |
| +1-methylpiperazine | 19.7(b) ± 2.4 | 13.2(c) ± 4.6 |

The data in Table 6 indicated that the effectiveness of these inhibitors (or repellents) was surprisingly not limited to a single species of mosquito. Thus, the data in Table 6 indicated that these compounds were also effective against mosquitoes of the genus *Anopheles* which contains mosquitoes that are known for global transmission of the malaria parasite.

TABLE 7

Competitive bioassays of attractants and inhibitors examined for Table 5. Results for paired t-tests are reported for comparison of means. *Aedes aegypii* mosquitoes were used. The treatments were (B) 3 compound attractant blend, (1-MPZ) 1-methylpiperazine, (4-MM) 4-methylmorpholine, (1-M-4-OPZ) 1-methyl-4-octylpiperazine. *indicates no significant difference in the treatments at the 0.05 level.

| Treatment 1 | Attraction mean ± SE (%) | Treatment 2 | Attraction mean ± SE (%) | t | P |
|---|---|---|---|---|---|
| B + (1-MPZ) | 4.6 ± 1.5 | B + (1-M-4-OPZ) | 24.5 ± 4.4 | 4.06 | 0.0097 |
| B + (1-MPZ)* | 5.4 ± 1.3 | B + (4-MM)* | 8.0 ± 1.1 | 1.54 | 0.1825 |
| B + (1-MPZ) + (4-MM) | 4.6 ± 0.8 | B | 29.9 ± 5.8 | 4.52 | 0.0063 |
| B + (1-MPZ) + (4-MM)* | 4.7 ± 1.8 | B + (4-MM)* | 5.1 ± 1.8 | 0.25 | 0.8114 |
| B + (1-MPZ) + (4-MM)* | 5.4 ± 1.8 | B + (1-MPZ)* | 5.1 ± 1.1 | 0.125 | 0.9051 |

From Table 7, competitive tests with *Ae. aegypti* demonstrated that 1-MPZ was suprisingly more effective than 1-methyl-4-octylpiperazine at inhibiting mosquitoes. For this mosquito species, 4-methylmorpholine surprisingly inhibited as well as 1-MPZ and combination of these two provided no further benefit over that provided by each compound introduced as the sole inhibitor.

TABLE 8

Competitive bioassays of attractants and inhibitors examined for Table 5. Results for paired t-tests were reported for comparison of means. *Anopheles albimanus* mosquitoes were used. The treatments were (B) 3 compound attractant blend, (1-MPZ) 1-methylpiperazine, and (4-MM) 4-methylmorpholine.

| Treatment 1 | Attraction mean ± SE (%) | Treatment 2 | Attraction mean ± SE (%) | t | P |
| --- | --- | --- | --- | --- | --- |
| B + (1-MPZ) + (4-MM)* | 5.2 ± 1.6 | B + (1-MPZ)* | 9.7 ± 3.3 | 1.16 | 0.2984 |
| B + (1-MPZ) + (4-MM)* | 10.3 ± 1.1 | B + (4-MM)* | 5.2 ± 2.0 | 2.16 | 0.0835 |
| B + (1-MPZ) + (4-MM) | 6.8 ± 1.3 | B | 25.9 ± 3.0 | 7.366 | <0.001 |

From Table 8, competitive tests with *An. albimanus* demonstrated that combinations of 1-MPZ and 1-methyl-4-octylpiperazine provided no further benefit over that provided by each compound introduced as the sole inhibitor and that the combination of inhibitor chemicals was clearly effective at reducing host-finding abilities of these mosquitoes by comparison of the attractant blend with the inhibitors to the attractant blend without addition of inhibitors

TABLE 9

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
| --- | --- | --- | --- | --- |
| 1 | homopiperazine 1,4-diazepane HPZ | 505-66-8 | 4.5(a) ± 1.1 | 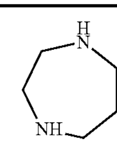 |
| 2 | 1-methylhomopiperazine 1-methyl-1,4-diazepane 1-HPZ | 4318-37-0 | 5.4(a) ± 0.6 | 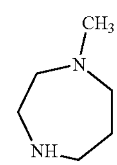 |
| 3 | 1-methylpyrrrolidine 1-MPR | 1220-94-5 | 6.6(a) ± 1.5 | 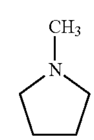 |
| 4 | (R)-(−)-2-methylpiperazine R-2-MPZ | 73336-86-6 | 6.8(a) ± 1.6 | 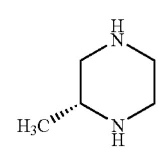 |
| 5 | (S)-(+)-2-methylpiperazine S-2-MPZ | Unknown | 7.0(a) ± 1.9 | 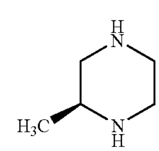 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 6 | 2-methylpiperazine (Mixture) 2-MPZ | 109-07-9 | 7.3(a) ± 3.0 | 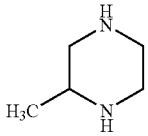 |
| 7 | 1-methylpiperazine 1-MPZ | 109-01-3 | 7.9(a) ± 1.4 | 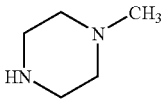 |
| 8 | pyrrolidine PR | 123-75-1 | 8.3(a) ± 1.0 | 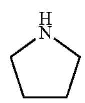 |
| 9 | 1-methylpiperidine 1-MPD | 626-67-5 | 9.3(a) ± 1.4 | 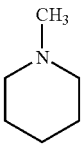 |
| 10 | piperidine PD | 110-89-4 | 9.3(a) ± 0.8 | 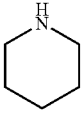 |
| 11 | 1-ethylpiperazine 1-EPZ | 5308-25-6 | 11.6(a) ± 2.6 | 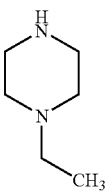 |
| 12 | 1-methylimidazolidine 1-MIM | unknown | 11.7(a) ± 2.1 | 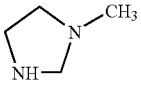 |
| 13 | 1-methylthiomorpholine 1-MTM | 55675-72-4 | 13.6(a) ± 2.6 | 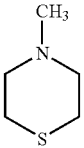 |
| 14 | 1,4-dimethylpiperazine 1,4-MPZ | 106-58-1 | 14.2(a) ± 5.3 | 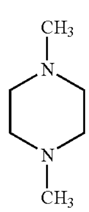 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 15 | homopiperidine hexamethyleneimine azepane HPD | 111-49-9 | 16.0(a) ± 2.0 | 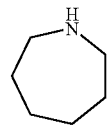 |
| 16 | Imidazolidine IM | 504-74-5 | 16.2(ab) ± 3.5 | 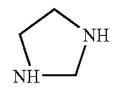 |
| 17 | 4-methylpiperidine 4-MPD | 626-58-4 | 16.6(ab) ± 2.4 | 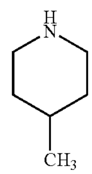 |
| 18 | thiomorpholine TM | 123-90-0 | 16.7(ab) ± 1.9 | 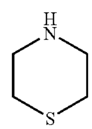 |
| 19 | 1-amino-4-methylpiperazine 4-methylpiperazine-1-amine 1-A-4MPZ | 6928-85-4 | 20.7(ab) ± 4.9 | 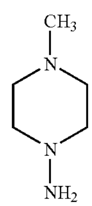 |
| 20 | 4-methylmorpholine 4-MM | 109-02-4 | 23.5(ab) ± 3.2 | 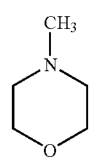 |
| 21 | azocane heptamethyleneimine AZO | 1121-92-2 | 31.7(b) ± 3.9 | 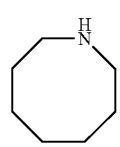 |
| 22 | 2,6-dimethylpiperazine 2,6-MPZ | 108-49-6 | 32.1(bc) ± 7.3 | 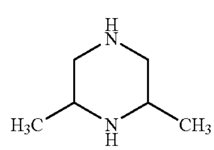 |
| 23 | 2,5-dimethylpiperazine 2,5-MPZ | 2815-34-1 | 39.7(c) ± 6.8 | 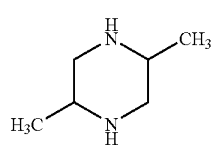 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 24 | piperazine PZ | 110-85-0 | 41.4(c) ± 8.8 | 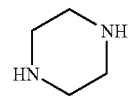 |
| 25 | 1,4-bis(2-hydroxyethyl)piperazine 2,2'-piperazine-1,4-diyldiethanol 1,4-2HEPZ | 122-96-3 | 73.3(d) ± 6.8 | 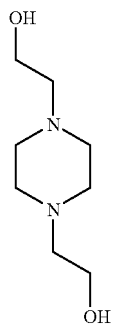 |
| 26 | 2-methyl-2-Imidazolinone 2-methyl-4,5-dihydro-1H-imidazole 2-MIZO | 534-26-9 | 76.0(d) ± 6.8 | 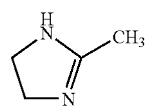 |
| 27 | 1-methylimidazole 1-MIZ | 616-47-1 | 76.9(d) ± 3.4 | 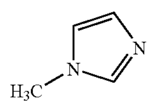 |
| 28 | 1-piperazine-carboxaldehyde piperazine-1-carbaldehyde 1-PZC | 7755-92-2 | 77.0(d) ± 3.5 | 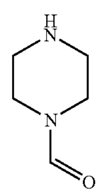 |
| 29 | 1-(2-methoxyphyenyl) piperazine 1-2MPPZ | 35386-24-4 | 77.1(d) ± 5.5 | 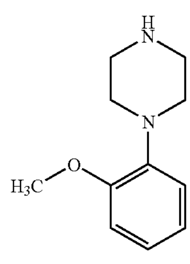 |
| 30 | 1-(3-methoxyphenyl) piperazine 1-3MPPZ | 16015-71-7 | 78.3(d) ± 3.2 | 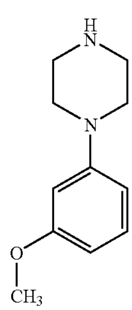 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|------|-------|--------------------------|-----------|
| 31 | 1-phenylpiperazine 1-PPZ | 92-54-6 | 78.9(d) ± 4.8 | 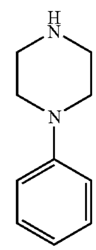 |
| 32 | 1-accetylpiperazine 1-APZ | 13889-98-0 | 80.2(d) ± 5.1 | 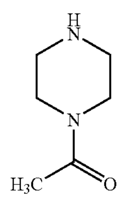 |
| 33 | imidazole IZ | 288-32-4 | 80.7(d) ± 6.8 | 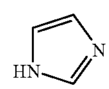 |
| 34 | methyl-4-morpholinepropionate M-4MP | 33611-43-7 | 81.7(d) ± 4.5 | 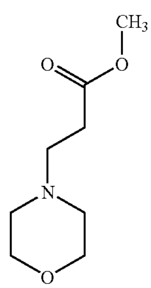 |
| 35 | Blend | n/a | 82.0(d) ± 2.8 | n/a |
| 36 | 1,4-di-p-tolylpiperazine 1,4-TPZ | Unknown | 84.7(d) ± 3.3 | 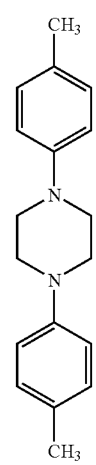 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 37 | ethyl piperazine-1-carboxylate<br>E-1PZC | 120-43-4 | 85.0(d) ± 4.4 | 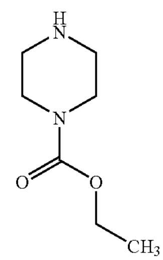 |
| 38 | 1-(2-pyridyl)piperazine<br>1-pyridin-2ylpiperazine<br>1-2PyPZ | 34803-66-2 | 85.3(d) ± 2.2 | 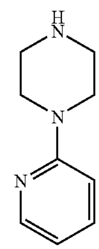 |
| 39 | 1-BOC-piperazine<br>t-Butyl piperazine-1-carboxylate<br>t-BPZC | 57260-71-6 | 85.6(d) ± 3.3 | 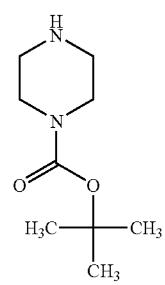 |
| 40 | 1,4-dinitropiperazine<br>1,4-DNPZ | Unknown | 87.3(d) ± 3.0 | 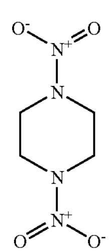 |
| 41 | 1-methylpiperazine dihydrochloride<br>1MPZ-2HCl | 34352-59-5 | 89.0(d) ± 2.6 | 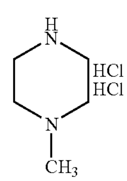 |
| 42 | 1-propylpiperazine dihydrobromidde<br>1PrPZ-2HBr | 64262-23-3 | 90.2(d) ± 2.1 | 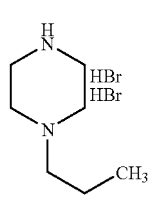 |

TABLE 9-continued

Comparison of host-seeking inhibition in Aedes aegypti mosquitoes from 50 μL of selected heterocycles combined with 500 μL of the 3-compound attractant blend as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 43 | 3-methylpiperazin-2-one 3M2PZO | Unknown | 90.9(d) ± 1.0 | 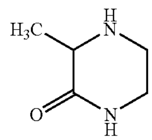 |
| 44 | pyrazine PY | 290-37-9 | 91.1(d) ± 1.5 | 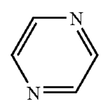 |
| 45 | a-[(4-methylpiperazin-1-yl)methyl]-w-piperazin-1-ylpoly(piperazine-1,4-diylmethylene) MPZ-MPZ (Polymer) | Unknown | 91.9(d) ± 2.5 | 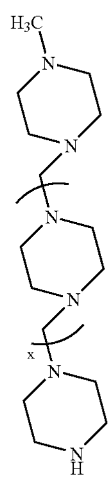 |
| 46 | 1-methylhomopiperidine 1-methylazepane 1-MHPD | 1192-95-6 | 93.9(d) ± 2.5 | 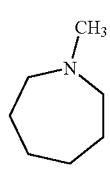 |

In Table 9 there were relatively large difference in response between #24 piperazine (41.4%) to #25 1,4-bis (2-hydroxyethyl)piperazine-2,2'-1,4-diyldiethanol (73%). The 73% response level of this compound level was not a significant statistical difference from the 82% of the blend average when candidate inhibitors were present. This indicated that although the ability of these compounds may differ within a small range, their effect was obvious in this type of bioassay.

The data in Table 10 confirmed that these compounds surprisingly work across species and genera of mosquitoes. A subset of the inhibitors was chosen and examined with *An. albimanus* mosquitoes. Although the relative effectiveness of these differed within this set, piperazine was still the least effective (and statistically significant inhibition compared to the blend). Note also, the blend in this case was a binary blend that historically results in the greatest attraction. (U.S. Pat. No. 6,257,953).

TABLE 10

Comparison of host-seeking inhibition in Anopheles albimanus mosquitoes from 400 µL (black cap release) of selected heterocycles combined with the 1 mL of methylene chloride with 200 µg L-lactic acid (white cap) as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 1 | 1-methylpiperidine<br>1-MPD | 626-67-5 | 10.3(a) ± 2.7 | 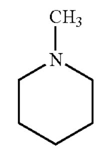 |
| 2 | pyrrolidine<br>PR | 123-75-1 | 10.5(a) ± 2.4 | 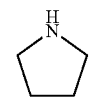 |
| 3 | homopiperidine<br>hexamethyleneimine<br>azepane<br>HPD | 111-49-9 | 13.8(a) ± 3.6 | 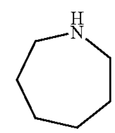 |
| 4 | 1-methylpyrrolidine<br>1-MPR | 1220-94-5 | 14.7(a) ± 3.0 | 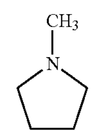 |
| 5 | piperidine<br>PD | 110-89-4 | 15.0(a) ± 4.0 | 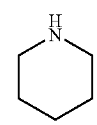 |
| 6 | azocane<br>heptamethyleneimine<br>AZO | 1121-92-2 | 17.7(a) ± 4.2 | 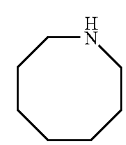 |
| 7 | 1-methylpiperazine<br>1-MPZ | 109-01-3 | 30.2(ab) ± 9.2 | 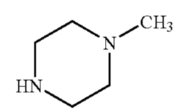 |
| 8 | 1-methylhomopiperazine<br>1-methyl-1,4-diazepane<br>1-HPZ | 4318-37-0 | 39.8(bc) ± 8.9 | 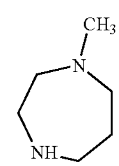 |
| 9 | 1-methylimidazolidine<br>1-MIM | unknown | 40.6(bc) ± 6.8 | 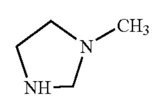 |

TABLE 10-continued

Comparison of host-seeking inhibition in Anopheles albimanus mosquitoes from 400 μL (black cap release) of selected heterocycles combined with the 1 mL of methylene chloride with 200 μg L-lactic acid (white cap) as the standard attractant. Bioassays were conducted in non-competitive mode. Values with the same letter are not significantly different at the 0.05 level.

| # | Name | CAS # | Attraction Mean ± SE (%) | Structure |
|---|---|---|---|---|
| 10 | homopiperazine 1,4-diazepane HPZ | 505-66-8 | 47.9(cd) ± 9.5 | 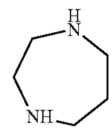 |
| 11 | Imidazolidine IM | 504-74-5 | 50.1(cd) ± 5.8 | 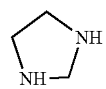 |
| 12 | 1-methylthiomorpholine 1-MTM | 55675-72-4 | 55.9(d) ± 4.3 | 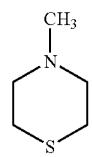 |
| 13 | 1-methylhomopiperidine 1-methylazepane 1-MHPD | 1192-95-6 | 58.4(d) ± 5.8 | 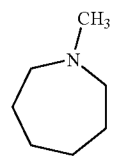 |
| 14 | piperazine PZ | 110-85-0 | 59.6(d) ± 7.5 | 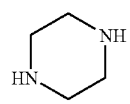 |
| 15 | Blend L-lactic acid + dichloromethane | | 73.3(e) ± 3.2 | |

Procedure for preparation of 1-Methyl imidazolidine: N-Methylethylenediamine (1 g, 13.5 mmol)was added to a suspension of paraformaldehyde (0.4 g 13.5 mmol), K$_2$CO$_3$ (6.4 g, 47.2 mmol) and MgSO$_4$ (5.6 g, 47.2 mmol) in CHCl$_3$ (25 mL) under argon at room temperature. After stirring for 18 h, the mixture was filtered, evaporated and purified by column chromatography on neutral alumina, eluting with CHCl$_3$-MeOH (9:1), to give the N-Metlylimidazolidine (70%).

Procedure for preparation of imidazolidine: Ethylenediamine (1 g, 16.6 mmol) was added to a suspension of paraformnaldehyde (0.49 g 16.6 mmol), K$_2$CO$_3$ (8.0 g, 58.3 mmol) and MgSO$_4$ (7.0 g, 58.8 mmol) in CHCl$_3$ (30 mL)under argon at room temperature. After stirring for 18 h, the mixture was filtered, evaporated and purified by column chromatography on neutral alumina, eluting with CHCl$_3$-MeOH (2:8), to give the imidazolidine (71%).

Procedure for preparation of 1-Methyl thiomorplioline: Thiomorpholine (1.0 g, 9.7 mmol) was added to a stirred solution of NaH (0.27 g, 11.6 mmol) in dry THF (20 mL), under argon at 0° C. After 30 min methyliodide (2.0 g, 14.5 mmol) was added and stirred the reaction mixture for 1 h. at room temperature. Then the reaction mixture was cooled to 0° C. and quenched with small portion of ice and extracted with ethylacetate. Organic layer was washed with saturated NaCl solution and dried over NaSO$_4$, evaporated under reduced pressure, purified by column chromatography on neutral alumina, eluting with CHCl$_3$-MeOH (95:5), to give the 1-methylthiomorpholine (78%).

Procedure for preparation of 1-Methyl homopiperidine: Hoopiperidine (1.0 g, 10.1 mmol) was added to a stirred solution of NaH (0.29 g, 12.1 mmol) in dry THF (20 mL), under argon at 0° C. After 30 min methyliodide (2.1 g, 15.15 mmol) was added and stirred the reaction mixture for 1 h. at room temperature. Then the reaction mixture was cooled to 0° C. and quenched with small portion of ice and extracted with etlhylacetate. Organic layer was washed with saturated NaCl solution and dried over NaSO$_4$, evaporated under reduced pressure, purified by column chromatography on neutral alumina, eluting with CHCl$_3$-MeOH (95:5), to give the 1-methylhomopiperidine (75%).

All of the references cited herein, including U.S. Patents, are incorporated by reference in their entirety. Also incorporated by reference in their entirety are the following references: Bernier, U. R., et al., J. Med. Entomol., 42: 306-311 (2005); Bernier, U. R, et al., Anal. Chem., 72: 747-756 (2000); Bernier, U. R., et al., Human Emanations and Related Natural Compounds that Inhibit Mosquito Host-Finding Ability, In Insect Repellents: Principles, Methods, and Uses, Debboun, M., Frances, S., Strickman, D., (Eds.), 2006, CRC Press: Boca Raton, Fla.; Bernier, U. R., et al., J. Am. Mosq. Control Assoc., 18: 186-195 (2002); Birkett, M. A., et al., Med. Vet. Entomol., 18: 313-322 (2004); Bosch, O. J., et al., Chem. Senses, 25: 323-330 (2000); Constantini, C., et al., Med. Vet. Entomol., 15: 259-266 (2001); Douglas III, H. D., et al., Naturwissenschaften., 88: 330-332 (2001); Douglas III, H. D., et al., J. Chem. Ecol., 30: 1921-1935 (2004); Douglas III, H. D., et al., J. Med. Entomol., 42: 647-651 (2005); Gouck, H. K., et al., I. Esters. J. Econ. Entomol., 60: 1587-1590 (1967); Kline, D. L., et al., J. Med. Entomol., 40: 463-467 (2003); Schreck, C. E., et al., J. Econ. Entomol., 63: 1576-1578 (1970); Skinner, W. A, et al., Science, 149: 305-306 (1965); Smallegange, R. C., et al., Chem. Senses., 30: 145-152 (2005); Torr, S. J., et al., Bull. Entomol. Res., 86: 609 (1996); Wirtz, R. A., et al., Mosq. News., 40: 432-439 (1980); Wright, R. H., et al., Can. Entomol., 103: 627-630 (1971).

Also incorporated by reference in their entirety are the following U.S. Patents: U.S. Pat. Nos. 6,267,953; 6,362,235; 6,800,479; 6,953,814.

Thus, in view of the above, the present invention concerns (in part) the following:

A method for repelling arthropods, said method comprising (or consisting essentially of or consisting of) treating an object or area with an arthropod repelling effective amount of at least one compound having the formula

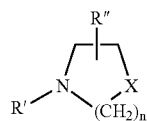

wherein X is O, S, NH, N-NH$_2$, N-CH$_3$ or C$_2$, R' is H or alkyl, R" is alkyl, and n is 0, 1, 2, 3 or 4.

The above method wherein said compound is selected from the group consisting of homopiperazine, 1-methylhomopiperazine 1-methylpyrrolidine, (R)-(−)-2-methylpiperazine, (S)-(+)-2-methylpiperazine, 2-methylpiperazinie, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylhomopiperidine, and mixtures thereof, optionally including a carrier material or carrier. The above method wherein the compound is homopiperazine. The above method wherein the compound is not homopiperazine. The above method wherein the compound is 1-metlylhomopiperazine. The above method wherein the compound is not 1-methylhomopiperazine. The above method wherein the compound is 1-methylpyrrolidine. The above method wherein the compound is not 1-methylpyrrolidine. The above method wherein the compound is (R)-(−)-2-methylpiperazine. The above method wherein the compound is not (R)-(−)-2-methylpiperazine. The above method wherein the compound is (S)-(+)-2-methylpiperazine. The above method wherein the compound is not (S)-(+)-2-methylpiperazine. The above method wherein the compound is 2-methylpiperazine. The above method wherein the compound is not 2-methylpiperazine. The above method wherein the compound is 1-methylpiperazine. The above method wherein the compound is not 1-methylpiperazine. The above method wherein the compound is pyrrolidine. The above method wherein the compound is not pyrrolidine. The above method wherein the compound is 1-methylpiperidine. The above method wherein the compound is not 1-methylpiperidine. The above method wherein the compound is piperidine. The above method wherein the compound is not piperidine. The above method wherein the compound is 1-ethylpiperazine. The above method wherein the compound is not 1-ethylpiperazine. The above method wherein the compound is 1-methylimidazolidine. The above method wherein the compound is not 1-methylimidazolidine. The above method wherein the compound is 1-methylthiomorpholine. The above method wherein the compound is not 1-methylthiomorpholine. The above method wherein the compound is 1,4-dimethylpiperazine. The above method wherein the compound is not 1,4-dimethylpiperazine. The above method wherein the compound is homopiperidine. The above method wherein the compound is not homopiperidine. The above method wherein the compound is imididazolidine. The above method wherein the compound is not imididazolidine. The above method wherein the compound is 4-methylpiperidine. The above method wherein the compound is not 4-methylpiperidine. The above method wherein the compound is thiomorpholine. The above method wherein the compound is not thiomorpholine. The above method wherein the compound is 1-amino-4-methylpiperazine. The above method wherein the compound is not 1-amino-4-methylpiperazine. The above method wherein the compound is 4-methylmorpholine. The above method wherein the compound is not 4-methylmorpholine. The above method wherein the compound is azocane. The above method wherein the compound is not azocane. The above method wherein the compound is 2,6-dimethylpiperazine. The above method wherein the compound is not 2,6-dimethylpiperazine. The above method wherein the compound is 2,5-dimethylpiperazine. The above method wherein the compound is not 2,5-dimethylpiperazine. The above method wherein the compound is piperazine. The above method wherein the compound is not piperazine. The above method wherein the compound is 1-methylhomopiperidine. The above method wherein the compound is not 1-methylhomopiperidine.

A method for producing anosmia or hyposmia in arthropods, said method comprising (or consisting essentially of or consisting of) treating an object or area with an anosmia or hyposmia producing effective amount of at least one compound having the formula

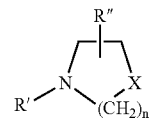

wherein X is O, S, NH, N-NH$_2$, N-CH$_3$ or CH$_2$, R' is H or alkyl, R" is alky, and n is 0, 1, 2, 3 or 4. The above method wherein said compound is selected from the group consisting of homopiperazine, 1-methylhomopiperazine, 1-methylpyrrolidiine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylhomopiperidine, and mixtures thereof, optionally including a carrier material or carrier. The above method wherein the compound is homopiperazine. The above method wherein the compound is not homopiperazine. The above method wherein the compound is 1-methylhomopiperazine. The above method wherein the compound is not 1-methylhomopiperazine. The above method wherein the compound is 1-methylpyrrolidine. The above method wherein the compound is not 1-methylpyrrolidine. The above method wherein the compound is (R)-(−)-2-methylpiperazine. The above method wherein the compound is not (R)-(−)-2-methylpiperazine. The above method wherein the compound is (S)-(+)-2-methylpiperazine. The above method wherein the compound is not (S)-(+)-2-methylpiperazine. The above method wherein the compound is 2-methylpiperazine. The above method wherein the compound is not 2-methylpiperazine. The above method wherein the compound is 1-methylpiperazine. The above method wherein the compound is not 1-methylpiperazine. The above method wherein the compound is pyrrolidine. The above method wherein the compound is not pynolidine. The above method wherein the compound is 1-methylpiperidine. The above method wherein the compound is not 1-methylpiperidine. The above method wherein the compound is piperidine. The above method wherein the compound is not piperidine. The above method wherein the compound is 1-ethlypiperazine. The above method wherein the compound is not 1-ethylpiperazine. The above method wherein the compound is 1-methylimidazolidine. The above method wherein the compound is not 1-methylimidazolidine. The above method wherein the compound is 1-methylthiomorpholine. The above method wherein the compound is not 1-methylthiomorpholine. The above method wherein the compound is 1,4-dimethylpiperazine. The above method wherein the compound is not 1,4-dimethylpiperazine. The above method wherein the compound is homopiperidine. The above method wherein the compound is not homopiperidine. The above method wherein the compound is imididazolidine. The above method wherein the compound is not imididazolidine. The above method wherein the compound is 4-methylpiperidine. The above method wherein the compound is not 4-methylpiperidine. The above method wherein the compound is thromorpholine. The above method wherein the compound is not thiomorpholine. The above method wherein the compound is 1-amnino-4-methylpiperazine. The above method wherein the compound is not 1-amino-4-methylpiperazine. The above method wherein the compound is 4-methylmorpholine. The above method wherein the compound is not 4-methylmorpholine. The above method wherein the compound is azocane. The above method wherein the compound is not azocane. The above method wherein the compound is 2,6-dimethylpiperazine. The above method wherein the compound is not 2,6-dimethylpiperazine. TIhe above method wherein the compound is 2,5-dimethylpiperazine. The above method wherein the compound is not 2,5-dimethylpiperazine. The above method wherein the compound is piperazine. The above method wherein the compound is not piperazine. The above method wherein the compound is 1-methylhomopiperidine. The above method wherein the compound is not 1-methylhomopiperidine.

A method for reducing the ability of arthropods to locate a host, said method comprising (or consisting essentially of or consisting of) treating an object or area with an effective amount (amount effective to reduce the ability of arthropods to locate a host) of at least one compound having the formula

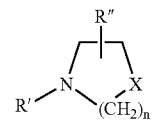

wherein X is O, S, NH, N-NH$_2$, N-CH$_3$ or CH$_2$, R' is H or alkyl, R" is alkyl, and n is 0, 1, 2, 3 or 4. The above method wherein said compound is selected from the group consisting of homopiperazine, 1-methylhomopiperazine, 1-methylpyrrolidine, (R)-(−)-2-methylpiperazine, (S)-(+)-2-methylpiperazine, 2-methylpiperazine 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, 1-methylhomopiperidine, and mixtures thereof, optionally including a carrier material or carrier. The above method wherein the compound is homopiperazine. The above method wherein the compound is not homopiperazine. The above method wherein the compound is 1-methylhomopiperazine. The above method wherein the compound is not 1-methylhomopiperazine. The above method wherein the compound is 1-methylpyrrolidine. The above method wherein the compound is not 1-methylpyrrolidine. The above method wherein the compound is (R)-(−)-2-methylpiperazine. The above method wherein the compound is not (R)-(−)-2-methylpiperazine. The above method wherein the compound is (S)-(+)-2-methylpiperazine. The above method wherein the compound is not (S)-(+)-2-methylpiperazine. The above method wherein the compound is 2-methylpiperazine. The above method wherein the compound is not 2-methylpiperazine. The above method wherein the compound is 1-methylpiperazine. The above method wherein the compound is not 1-methylpiperazine. The above method wherein the compound is pyrrolidine. The above method wherein the compound is not pyrrolidine. The above method wherein the compound is 1-methylpiperidine. The above method wherein the compound is not 1-methylpiperidine. The above method wherein the compound is piperidine. The above method wherein the compound is not piperidine. The above method wherein the compound is 1-ethylpiperazine. The above method wherein the compound is not 1-ethylpiperazine. The above method wherein the compound is 1-methylimidazolidine. The above method wherein the compound is not 1-methylimidazolidine. The above method wvherein the compound is 1-methylthiomorpholine. The above method wherein the compound is not 1-methylthiomoi-pholine. The above method wherein the compound is 1,4-dimethylpiperazine. The above method wherein the compound is not 1,4-dimethylpiperazine. The above method wherein the compound is homopiperidine. The above method wherein the compound is not homopiperidine. The above method wherein the compound is imididazolidine. The above method wherein the compound is not imididazolidine. The above method wherein the compound is 4-methylpiperidine. The above method wherein the compound is not 4-methylpiperidine. The above method wherein the compound is thiomorpholine. The above method wherein the compound is not thiomorpholine. The above method wherein the compound is amino-4-methylpiperazine. The above method wherein the compound is not 1-amino-4-methylpiperazine. The above method wherein the compound is 4-methylmorpholine. The above method wherein the compound is not 4-methylmorpholine. The above method wherein the compound is azocane. The above method wherein the compound is not azocane. The above method wherein the compound is 2,6-dimethylpiperazine. The above method wherein the compound is not 2,6-dimethylpiperazine. The above method wherein the compound is 2,5-dimethylpiperzine. The above method wherein the compound is not 2,5-dimethylpiperazine. The above method wherein the compound is piperazine. The above method wherein the compound is not piperazine. The above method wherein the compound is 1-methylhomopiperidine. The above method wherein the compound is not 1-methylhomopiperidine.

A composition comprising at least one member selected from the group consisting of imididazolidine, 1-methylimidazolidine, 1-methylhomopiperidine, 1-methyl thiomorpholine, and mixtures thereof, and optionally including a carrier material or carrier.

Imididazolidine, optionally including a carrier material or carrier.

1-methylimidazolidine, optionally including a carrier material or carrier.

1-methylhomopiperidine, optionally including a carrier material or carrier.

1-Methyl thiomorpholine, optionally including a carrier material or carrier.

A composition comprising at least two compounds having the formula

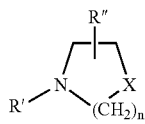

wherein X is O, S, NH, N-NH$_2$, N-CH$_3$ or CH$_2$, R' is H or alkyl, R' is alkyl, n is 0, 1, 2, 3 or 4, and mixtures thereof, optionally including a carrier material or carrier. The above composition, wherein said compounds are selected from the group consisting of homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine. 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-mnethylpiperazine, 4-methylmorpholine, azocane, 2,6-dimethylpiperazine, 2,5-dimethylpiperazine, piperazine, 1-methylhomopiperidine, and mixtures thereof, optionally including a carrier material or carrier. The above composition wherein one of the compounds is homopiperazine. The above composition wherein one of the compounds is not homopiperazine. The above composition wherein one of the compounds is 1-methylhomopiperazine. The above composition wherein one of the compounds is not 1-methylhomopiperazine. The above composition wherein one of the compounds is 1-methylpyrrolidine. The above composition wherein one of the compounds is not 1-methylpyrrolidine. The above composition wherein one of the compounds is (R)-(−)-2-methylpiperazine. The above composition wherein one of the compounds is not (R)-(−)-2-methylpiperazine. The above composition wherein one of the compounds is (S)-(+)-2-methylpiperazine. The above composition wherein one of the compounds is not (S)-(+)-2-methylpiperazine. The above composition wherein one of the compounds is 2-methylpiperazine. The above composition wherein one of the compounds is not 2-methylpiperazine. The above composition wherein one of the compounds is 1-methylpiperazine. The above composition wherein one of the compounds is not 1-methylpiperazine. The above composition wherein one of the compounds is pyrrolidine. The above composition wherein one of the compounds is not pyrrolidine. The above composition wherein one of the compounds is 1-methylpiperidine. The above composition wherein one of the compounds is not 1-methylpiperidine. The above composition wherein one of the compounds is piperidine. The above composition wherein one of the compounds is not piperidine. The above composition wherein one of the compounds is 1-ethylpiperazine. The above composition wherein one of the compounds is not 1-ethylpiperazine. The above composition wherein one of the compounds is 1-methylimidazolidine. The above composition wherein one of the compounds is not 1-methylimidazolidine. The above composition wherein one of the compounds is 1-methylthiomorpholine. The above composition wherein one of the compounds is not 1-methylthiomorpholine. The above composition wherein one of the compounds is 1,4-dimethylpiperazine. The above composition wherein one of the compounds is not 1,4-dimethylpiperazine. The above composition wherein one of the compounds is homopiperidine. The above composition wherein one of the compounds is not homopiperidine. The above composition wherein one of the compounds is imididazolidine. The above composition wherein one of the compounds is not imididazolidine. The above composition wherein one of the compounds is 4-methylpiperidine. The above composition wherein one of the compounds is not 4-methylpiperidine. The above composition wherein one of the compounds is thiomorpholine. The above composition wherein one of the compounds is not homopiperidine. The above composition wherein one of the compounds is 1-amino-4-methylypiperazine. The above composition wherein one of the compounds is not 1-amino-4-methylpiperazine. The above composition wherein one of the compounds is 4-methylmorpholine. The above composition wherein one of the compounds is not 4-methylmorpholine. The above composition wherein one of the compounds is azocane. The above composition wherein one of the compounds is not azocane. The above composition wherein one of the compounds is 2,6-dimethylpiperazine. The above composition wherein one of the compounds is not 2,6-dimethylpiperazine. The above composition wherein one of the compounds is 2,5-dimethylpiperazine. The above composition wherein one of the compounds is not 2,5-dimethylpiperazine. The above composition wherein one of the compounds is piperazine. The above composition wherein one of the compounds is not piperazine. The above composition wherein one of the compounds is 1-methylhomopiperidine. The above composition wherein one of the compounds is not 1-methylhomopiperidine.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:
1. A method for repelling blood-sucking insects, biting insects, ticks and mites, said method comprising treating an object or area with a repelling effective amount of at least one compound selected from the group consisting of homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, and mixtures thereof, including a carrier material or carrier.

2. The method according to claim 1, wherein said blood-sucking insects are selected from the group consisting of *Aedes aegypti, Anopheles albimanus*, and mixtures thereof.

3. A method for repelling blood-sucking insects, biting insects, ticks and mites, said method consisting essentially of treating an object or area with a repelling effective amount of at least one compound selected from the group consisting of homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, and mixtures thereof, including a carrier material or carrier.

4. The method according to claim 1, said method consisting of treating an object or area with a repelling effective amount of at least one compound selected from the group consisting of homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, and mixtures thereof, including a carrier material or carrier.

5. The method according to claim 1, wherein said method is a method for repelling blood-sucking insects.

6. The method according to claim 5, wherein said blood-sucking insects are selected from the group consisting of *Aedes aegypti, Anopheles albimanus*, and mixtures thereof.

7. The method according to claim 1, wherein said method is a method for repelling biting insects.

8. The method according to claim 1, wherein said method is a method for repelling ticks.

9. The method according to claim 1, wherein said method is a method for repelling mites.

10. A method for repelling mosquitoes, said method comprising treating an object or area with a repelling effective amount of at least one compound selected from the group consisting of homopiperazine, 1-methylhomopiperazine, 1-methylpyrrolidine, (R)-(−)-2-methylpiperazine, (S)-(+)-2-methylpiperazine, 2-methylpiperazine, 1-methylpiperazine, pyrrolidine, 1-methylpiperidine, piperidine, 1-ethylpiperazine, 1-methylimidazolidine, 1-methylthiomorpholine, 1,4-dimethylpiperazine, homopiperidine, imidazolidine, 4-methylpiperidine, thiomorpholine, 1-amino-4-methylpiperazine, 4-methylmorpholine, azocane, 2,6-dimethylpiperazine, 2,5-dimethylpiperazine, piperazine, and mixtures thereof, including a carrier material or carrier.

11. The method according to claim 10, wherein said mosquitoes are selected from the group consisting of *Aedes aegypti, Anopheles albimanus*, and mixtures thereof.

\* \* \* \* \*